United States Patent [19]

Piper et al.

[11] Patent Number: 4,725,687

[45] Date of Patent: Feb. 16, 1988

[54] 5-METHYL-5-DEAZA ANALOGUES OF METHOTREXATE AND N[10]-ETHYLAMINOPTERIN

[75] Inventors: James R. Piper; John A. Montgomery, both of Birmingham, Ala.; Francis M. Sirotnak, New York, N.Y.

[73] Assignees: Southern Research Institute, Birmingham, Ala.; Sloan-Kettering Institute for Cancer Research, New York, N.Y.

[21] Appl. No.: 856,388

[22] Filed: Apr. 28, 1986

[51] Int. Cl.[4] .................. C07D 471/04; A61K 31/505
[52] U.S. Cl. ..................................... 544/279; 546/287
[58] Field of Search .......................... 544/279; 514/258

[56] References Cited

U.S. PATENT DOCUMENTS 4,460,591  7/1984  DeGrow et al. ............... 514/258
4,536,575  8/1985  Temple et al. ................. 544/279

OTHER PUBLICATIONS

Su et al., J. Med. Chem., 1986, 29, 709–715.
Piper et al., J. Med. Chem., 1986, 29, 1080–1087.
Griusky et al., J. Med. Chem., 1980, 23, 327.
Edward C. Taylor et al., J. Org. Chem., vol. 48, No. 25, pp. 4852–4860 (1983).
"Synthesis of Fused Pyrimidines as Folate Antagonists", (1974) Elslager et al, *Lect. Heterocycl. Chem.*, vol. II, pp. S97–S133.
*Monatsch. Chem.*, Schmidt et al, vol. 108, pp. 895–900 (1977).

*Primary Examiner*—Donald G. Daus
*Assistant Examiner*—Barbara Cassatt
*Attorney, Agent, or Firm*—Roylance, Abrams, Berdo & Goodman

[57] ABSTRACT

It is disclosed that 5-methyl-5-deazamethotrexate and 5-methyl-5-deaza-10-ethylaminopterin are more than 10 times as potent as 5-deazamethotrexate in the L1210 cell growth inhibition test.

13 Claims, No Drawings

5-METHYL-5-DEAZA ANALOGUES OF METHOTREXATE AND N[10]-ETHYLAMINOPTERIN

BACKGROUND OF THE INVENTION

This invention relates to 5-methyl-5-deaza analogues of methotrexate and N[10]-ethylaminopterin and to the use of such compounds as antineoplastic agents.

Methotrexate (MTX) remains the only classical antifolate in established clinical use, and its use has continued to expand as new methods of administering the drug have been introduced and as other tumor types have been added to the list of those now being treated. MTX usage, however, suffers major limitations due to its toxic side effects and the development of resistance by tumor cells. Some tumors are naturally resistant to MTX while other acquire resistance after a period of response. Three factors known to contribute to drug resistance are (a) loss of the active-transport system by which MTX enters cells, (b) increased levels of dihydrofolate reductase (DHFR), the intracellular target of MTX, and (c) the presence of structurally altered DHFR having lower affinity for MTX. Another explanation of resistance may be offered in the recent description of a structurally altered DHFR from an MTX-resistant mutant cell line with unaltered affinity for MTX, but with greater capacity to reduce dihydrofolate than the DHFR from the parent MTX-sensitive cell line. MTX and aminopterin (AMT) have the following structures:

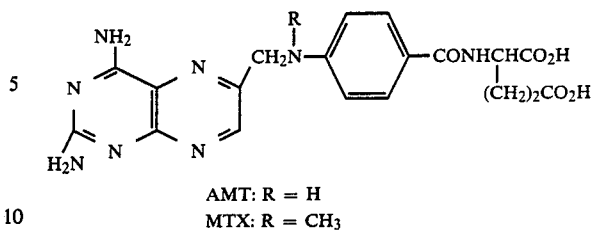

AMT: R = H
MTX: R = CH$_3$

As part of a program aimed toward the identification of new antifolate agents that exert greater therapeutic effectiveness against a broader spectrum of tumors than agents now available, antifolates are sought having favorably altered transport characteristics but still possessing tight binding affinity for DHFR. In studies aimed toward greater understanding of transport properties, differences have been observed between tumor and normal proliferative tissue in mediated cellular membrane transport of antifolates and in the intracellular γ-polyglutamylation of the agents. These biochemical parameters appear to be critical determinants for selective antitumor activity. In studies that document these differences, positions 5 and 10 on the classical antifolate-type molecular structure have been identified as sites where modification does not reduce binding to DHFR but does influence transport efficacy to favor inward flux into tumor cells and also intracellular γ-polyglutamylation resulting in greater accumulation in tumor cells than in normal cells.

In the discussion which follows, reference will be made to underlined numbers which identify compounds shown by structural formulas in Scheme I. Scheme I is as follows:

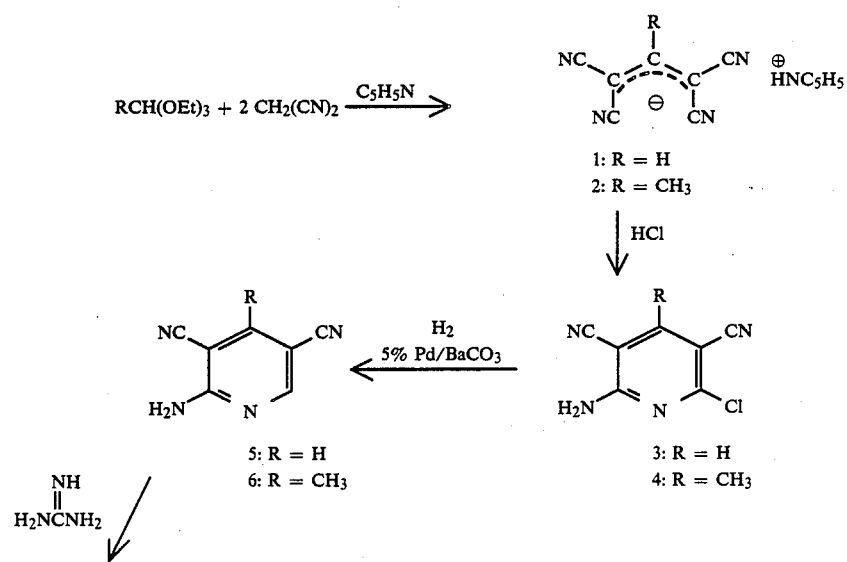

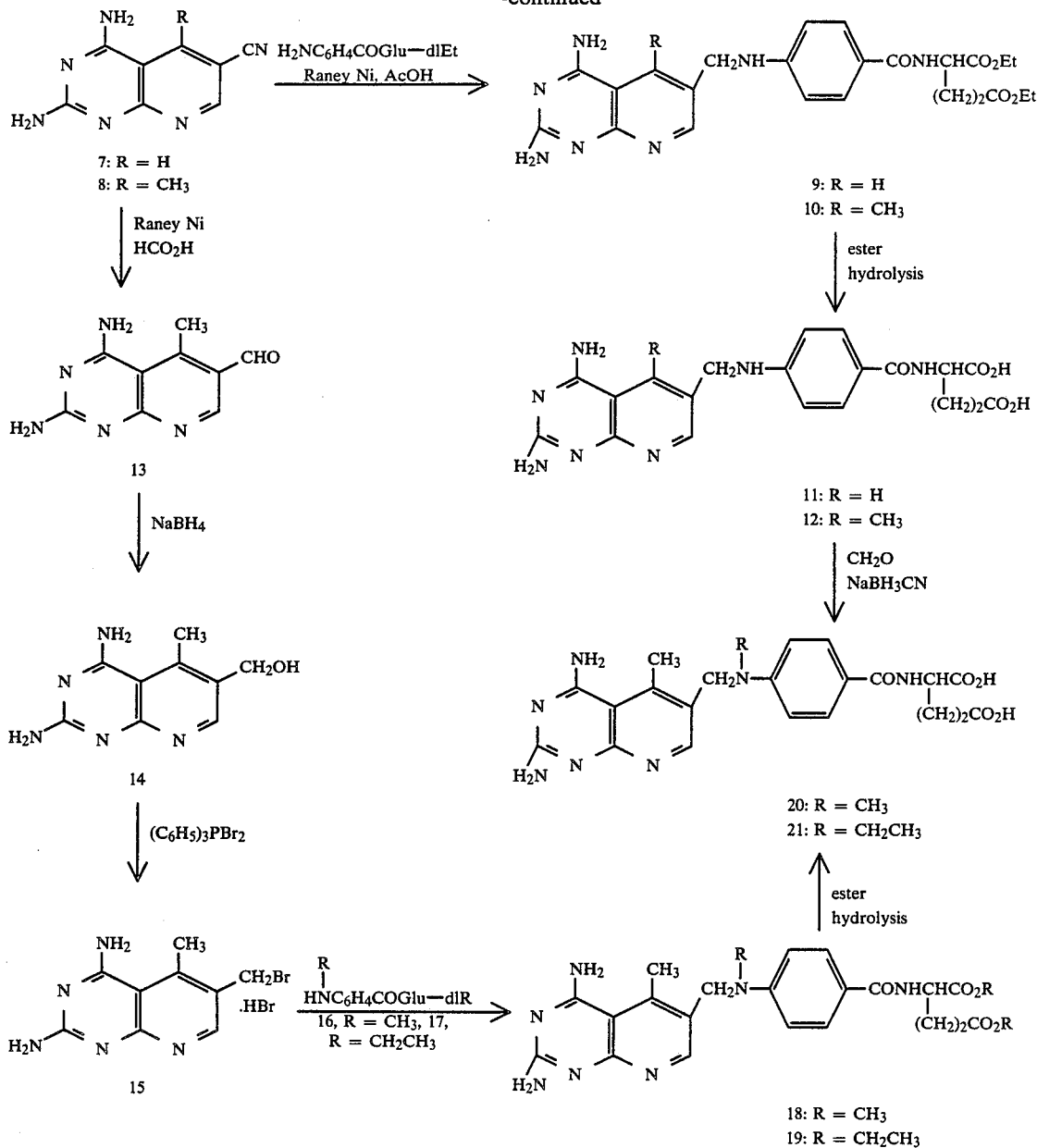

In Scheme I, compounds 3, 5, 7, 9, and 11 are disclosed by Elslager et al, "Synthesis of Fused Pyrimidines as Folate Antagonists", presented during the Fourth International Congress of Heterocyclic Chemistry, University of Utah, Salt Lake City, Utah, July 8–13, 1973; published in Lect. Heterocycl. Chem., Vol. II, pps. S-97 to S-132 (1974), see especially pps. S-120 to S-121. Schmidt et al, Monatsch. Chem., Vol. 108, pps. 895 to 900 (1977) teaches the preparation of 2-amino-6-chloro-3,5-dycano-(4-alkyl)-pyridines which includes compound 4 is Scheme I. Compounds 4, 6, 8, 10 and 12 of Scheme I are homologues of compounds disclosed by Elslager et al, supra; and compounds 12, 13, 14, 15, 18, 19, 20, and 21, are homologues of compounds disclosed by U.S. Pat. No. 4,536,575 to Temple et al.

BRIEF DESCRIPTION OF THE INVENTION

It has now been found that 5-methyl-5-deazamethotrexate (20) and 5-methyl-5-deaza-10-ethylaminopterin (21) are more than 10 times as potent as 5-deazamethotrexate in the L1210 cell growth inhibition test.

Referring now to Scheme I, compounds 3 and 4 were prepared by reported procedures, which proved to be readily adaptable to large-scale preparations. The reductive dechlorination Steps to give 5 and 6 were done in DMF—MeOH (N,N-dimethylformamide-methyl alcohol) solution containing 5% Pd on $BaCO_3$. This method differs slightly from the reported conversion of 3 to 5, which was done in DMF using $PdCl_2$ with $Et_3N$ (triethylamine) serving as the HCl scavenger. Annelation of the 2,4-diaminopyrimidine moiety by treatment of 5 and 6 with guanidine in refluxing EtOH (ethyl alcohol) followed. 2,4-Diaminopyrido[2,3-d]pyrimidine-6-carbonitrile (7) was obtained in 95% yield; starting 5 was no longer present in the reaction mixture after 24 hours according to TLC. The 5-methyl congener 8 formed less readily. Even after 5 days, some 6 was still present, but the unchanged material was easily removed during isolation of 8 in acceptable (58%) yield. Reductive condensation of 7 with diethyl N-(4-aminobenzoyl)-L-glutamate in 70% AcOH (acetic acid) solution in the presence of Raney Ni was done using a procedure similar to that reported for the reductive amination of the corresponding aldehyde. The procedure was adapted from the reported general method for the preparation of quinazoline (5,8-dideaza) analogues of AMT. The diethyl ester 9 thus formed proved to be identical with the sample previously reported. The reductive condensation was then applied to 8 to give the diethyl ester of the corresponding 5-methyl compound 10. The esters 9 and 10 were then hydrolyzed to give 5-dAMT (11) and 5-Me-5-dAMT (12). The methyl compound 12 was methylated at $N^{10}$ to give 5-methyl-5-deazamethotrexate (5-Me-5-dMTX, 20).

In order to extend the usefulness of this facile method, the nitrile 8 was converted by treatment with Raney Ni in aqueous $HCO_2H$ to the corresponding aldehyde 13, which was then reduced by $NaBH_4$ to give the hydroxymethyl compound 14. The 6-(bromomethyl) compound 15 was prepared by adaptation of the procedure used to prepare 6-(bromomethyl)-2,4-pteridinediamine hydrobromide reported by Piper et al, *J. Org. Chem.*, Vol. 42, page 208 (1977). The bromoethyl compound 15 was not obtained in pure form as was the pteridine analogue, but it proved to be suitable for effective synthetic use. Alkylation of dimethyl N-[4-(methylamino)benzoyl]-L-glutamate (16) with 15 in Me$_2$NAc (N,N-dimethylacetamide) afforded the ester 18, which was hydrolyzed to give the $N^{10}$-methyl analogue 20, identical with the sample prepared from 12 by reductive alkylation. Similarly, the $N^{10}$-ethyl analogue 21 was prepared via its diethyl ester 19 from 15 and diethyl N-[4-(ethylamino)benzoyl]-L-glutamate (17) thereby demonstrating the potential of 15 to prepare congeners modified in the $C^9$—$N^{10}$ bridge and presumably in the remainder of the N-benzoyl-L-glutamic acid moiety.

DETAILED DESCRIPTION OF THE INVENTION

The compounds of the invention form pharmaceutically acceptable salts with both organic and inorganic acids. Examples of suitable acids for salt formation are hydrochloric, sulfuric, phosphoric, acetic, citric, oxalic, malonic, salicyclic, malic, fumaric, succinic, ascorbic maleic, methanesulfonic, and the like. The salts are prepared by contacting the free base form with an equivalent amount of the desired acid in the conventional manner. The free base forms may be regenerated by treating the salt form with a base. For example, dilute aqueous base solutions may be utilized. Dilute aqueous sodium hydroxide, potassium carbonate, ammonia, and sodium bicarbonate solutions are suitable for this purpose. The free base forms differ from their respective salt forms somewhat in certain physical properties such as solubility in polar solvents, but the salts are otherwise equivalent to their respective free base forms for purposes of the invention.

The compounds of the invention also form pharmaceutically acceptable carboxylate salts by reacting a suitable base with one or more of the free carboxyl groups. Suitable bases include alkali metal or alkaline earth metal hydroxides or carbonates, for example, sodium hydroxide, potassium hydroxide, calcium hydroxide, magnesium hydroxide, and corresponding carbonates; and nitrogen bases such as ammonia and alkylamines such as trimethylamine and triethylamine.

The novel compounds of the present invention inhibit transplanted mouse tumor growth when administered in amounts ranging from about 5 mg to about 200 mg per kilogram of body weight per day. A preferred dosage regimen for optimum results would be from about 5 mg to about 50 mg per kilogram of body weight per day, and such dosage units are employed that a total of from about 350 mg to about 3.5 grams of the active compounds for a subject of about 70 kg of body weight are administered in a 24-hour period. This dosage regimen may be adjusted to provide the optimum therapeutic response. For example, several divided doses may be administered daily or the dose may be proportionally reduced as indicated by the exigencies of the therapeutic situation. A decided practical advantage is that the active compound may be administered in any convenient manner such as by the oral, intravenous, intramuscular or subcutaneous routes.

The active compounds may be orally administered, for example, with an inert diluent or with an assimilable edible carrier, or they may be enclosed in hard or soft shell gelatin capsules, or they may be compressed into tablets, or they may be incorporated directly with the food of the diet. For oral therapeutic administration, the active compounds may be incorporated with excipients and used in the form of ingestible tablets, buccal tablets, troches, capsules, elixirs, suspensions, syrups, wafers and the like. Such compositions and preparations should contain at least 0.1% of active compound. The percentage of the compositions and preparations may, of course, be varied and may conveniently be between about 2 and about 60% of the weight of the unit. The amount of active compound in such therapeutically useful compositions is such that a suitable dosage will be obtained. Preferred compositions or preparations according to the present invention are prepared so that an oral dosage unit form contains between about 5 and about 200 milligrams of active compound.

The tablets, troches, pills, capsules and the like may also contain the following: a binder such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to materials of the above type, a liquid carrier. Various other materials may be present as coatings or to otherwise modify the physical form of the dosage unit. For instance, tablets, pills or capsules may be coated with shellac, sugar or both. A syrup or elixir may contain the active compound, sucrose as a sweetening agent, methyl and propylparabens as preservatives, a dye and flavoring such as cherry or orange flavor. Of course, any material used in preparing any dosage unit form should be pharmaceutically pure and substantially non-toxic in the amounts employed. In addition, the active compounds may be incorporated into sustained-release preparations and formulations.

The active compounds may also be administered parenterally or intraperitoneally. Solutions of the active compound as a free base or pharmaceutically acceptable salt can be prepared in water suitably mixed with a surfactant such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), suitable mixtures thereof and vegetable oils. The proper fluidity can be maintained, for example, by the use of a coating such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filtered sterilization. Generally, dispersions are prepared by incorporating the various sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze-drying technique which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for ease of administration and uniformity of dosage. Dosage unit form as used herein refers to physically discrete units suitable as unitary dosage for the mammalian subjects to be treated; each unit containing a predetermined quantity of active material calculated to produce the desired therapeutic effect in association with the required pharmaceutical carrier. The specification for the novel dosage unit forms of the invention are dictated by and directly dependent on (a) the unique characteristics of the active material and the particular therapeutic effect to be achieved, and (b) the limitations inherent in the art of compounding such an active material for the treatment of disease in living subjects having a diseased condition in which bodily health is impaired as herein disclosed in detail.

The principal active ingredient is compounded for convenient and effective administration in effective amounts with a suitable pharmaceutically-acceptable carrier in dosage unit form as hereinbefore disclosed. A unit dosage form can, for example, contain the principal active compound in amounts ranging from about 0.1 to about 400 mg, with from about one to about 30 mg being preferred. Expressed in proportions, the active compound is generally present in from about 0.1 to about 400 mg/ml of carrier. In the case of compositions containing supplementary active ingredients, the dosages are determined by reference to the usual dose and manner of administration of the said ingredients.

The following examples illustrate the best modes known for carrying out this invention. In these examples, examinations by TLC were performed on Analtech precoated (250 $\mu$m) silica gel G(F) plates. HPLC assays were made with a Waters Associates ALC-242 liquid chromatograph equipped with a UV detector (254 nm) and the M-6000 pump using a 30×0.29 cm $C_{18}\mu$ Bondapak column. Purity assays were done using reverse-phase in the isocratic mode with a mobile phase consisting of $CH_3CN$ (10 or 15% by volume) in 0.1M NaOAc (sodium acetate) (pH3.6). Hydrolyses of esters were monitored using a 20 minute linear gradient system with the combination $CH_3CN$-0.1M NaOAc (pH 3.6) changing from 15% $CH_3CN$ to 50%. Melting points, unless indicated otherwise, were determined on a Mel-Temp apparatus and are uncorrected. Except where other conditions are specified, evaporations were performed with a rotary evaporator and an $H_2O$ aspirator. Products were dried in vacuo (<1 mm) at 22°-25° C. over $P_2O_5$ and NaOH pellets. Final products were dried and then allowed to equilibrate with ambient conditions of the laboratory. Analytical results indicated by element symbols were within ±0.4% of the theoretical values. The $^1H$ NMR spectral data reported were determined with a Nicolet NMC 300NB spectrometer (compound 20) and with a Varian XL-100-15 spectrometer (all others) using $Me_4Si$ (tetramethylsilane) as internal reference. Chemical shifts ($\delta$ in ppm) listed for multiplets were measured from the approximate centers, and relative integrals of peak areas agreed with those expected for the assigned structures. Mass spectra were recorded in the fast atom bombardment mode on a Varian MAT 311A mass spectrometer equipped with electron impact-field ionization/field desorption and fast atom bombardment ion sources. The UV spectra were determined with a Cary Model 17 spectrometer. Samples were first dissolved in 0.01N NaOH, and the solutions were then diluted tenfold with the medium given in the listings. Maxima are expressed in nanometers with the molar absorbance ($\epsilon \times 10^3$) given in parentheses. Molecular weights used in all calculations conform with the compositions listed with elemental analysis results. Elemental analyses are set forth in Table 1 following the examples. In this table, the calculated value is given first and the found value is given second.

EXAMPLE 1

2-Amino-6-chloro-3,5-pyridinedicarbonitrile (3) was prepared by the procedure of Schmidt et al, supra, in which a mixture of malononitrile, triethyl orthoformate, and pyridine in the molar ratio 2:1 was heated under reflux for 20 minutes to give crystalline pyridinium 1,1,3,3-tetracyanopropenide (1) which was then treated, without isolation, with concentrated HCl at 80° C. to give 3. Pure 3, mp∼200° C. (sublimation), was obtained in 58% yield [23.1 g from a run using 30.0 g (0.454 mol) of malononitrile and 0.227 mol each of triethyl orthoformate and pyridine] after recrystallization from DMF (1 L)-$H_2O$ (2 L) as described below for the recrystallization of methyl-substituted 4. The 3 thus obtained was homogeneous according to TLC ($CHCl_3$—MeOH, 2:1).

EXAMPLE 2

2-Amino-6-chloro-4-methyl-3,5-pyridinedicarbonitrile (4). A stirred solution of malononitrile (20.8 g, 0.424 mol), triethyl orthoacetate (35.0 g, 0.216 mol), and pyridine (86 mL) was refluxed for 35 minutes, cooled, and evaporated (bath to 50° C.). Treatment of the residue with concentrated HCl (240 mL) with stirring at 80° C. (bath temperature) for 45 minutes caused formation of 4 as an insoluble off-white solid. The mixture was cooled, and $H_2O$ (400 mL) was added before the solid was collected and washed successively with $H_2O$, EtOH and $Et_2O$ (ethyl ether). The solid was then dissolved in hot (80° C.) DMF (200 mL), and the clarified (Norit, Celite) solution was added to stirred $H_2O$ (400 mL) to cause precipitation of 4. The white solid was collected as before; yield 49% (19.8 g), homogeneous by TLC [cyclohexane-EtOAc (ethyl acetate), 1:1]; IR, $v_{max}^{KBr}$, $cm^{-1}$, 3351, 3329, 3175 ($NH_2$), 2230, 2222 (CN), 1652, 1567 (C=C, C=N). Although 4 has been reported in the literature as having mp 210° C., the pure product which was obtained in this example from three preparations did not have a distinct mp; samples in capillaries were observed to undergo change in crystalline modification near 230° C. to form colorless rods which did not melt below 270° C.

EXAMPLE 3

2-Amino-3,5-dicyanopyridine (5) was prepared from 3 using the procedure described below for the preparation of 5 except that 5 was recrystallised from MeCN [methyl cyanide; acetonitrile) (instead of EtOH). The yield was 73% (7.00 g from 12.0 g (67.2 mmol) of 3] of product homogeneous on TLC (cyclohexane-EtOAc, 1:1); mp 220° C. dec; $^1H$ NMR ($Me_2SO-d_6$) δ7.90 (s, $NH_2$), 8.40 and 8.58 (two d, 4-H and 6H, J=2 Hz).

EXAMPLE 4

2-Amino-4-methyl-3,5-pyridinedicarbonitrile (6). Hydrogenolysis of 4 (10.0 g, 52.0 mmol) in DMF (150 mL)-MeOH (75 mL) containing 5% Pd on $BaCO_3$ (10.0 g) was carried out in a Parr shaker with $H_2$ pressure kept near 3.5 $kg/cm^2$ (50 psi) for six hours. The mixture was then filtered (Celite mat), and evaporated to dryness (final conditions <1 mm, bath to 45° C.) The residue containing Ba salts which separated during the evaporation was stirred with $H_2O$ (100 mL) to give the $H_2O$-insoluble product (7.74 g). Recrystallization from EtOH (800 mL) then gave pure 6, mp 222°-223° C., in 86% yield (7.1 g); homogeneous by TLC (cyclohexane-EtOAc, 1:1); $^1H$ NMR ($Me_2SO-d_6$) δ2.50 (s, $CH_3$), 7.82 (s, $NH_2$), 8.50 (s, $C^2$—H).

EXAMPLE 5

2,4-Diaminopyrido[2,3-d]pyrimidine-6-carbonitrile (7). Guanidine·HCl (2.66 g, 27.8 mmol) was added to a solution of NaOMe (sodium methoxide) (1.50 g, 27.8 mmol) in absolute EtOH (180 mL). The mixture was stirred at 20°-23° C. for 15 minutes before 5 (2.00 g, 13.9 mmol) was added. After a 24-hour reflux period with rapid stirring, TLC (cyclohexane-EtOAc, 1:1) showed absence of 5. The solid filtered from the cooled mixture was washed on the funnel with $H_2O$ and EtOH; yield 95% (2.45 g). A sample of this material (1.0 g) was stirred with near-boiling $Me_2SO$ (dimethyl sulfoxide) (250 mL), and the slightly cloudy solution was filtered (Celite) to give a clear, pale-yellow filtrate which was then concentrated by evaporation in vacuo (to about 60 mL). Addition of EtOH (200 mL) gave 7 as a light yellow solid (880 mg); $^1H$ NMR ($Me_2SO-d_6$) δ6.97 (2, $NH_2$), 7.84 (s, $NH_2$), 8.87 and 8.91 (two d, 5-H and 7-H, J=2 Hz).

EXAMPLE 6

2,4-Diamino-5-methylpyrido[2,3-d]pyrimidine-6-carbonitrile (8). Dried and pulverized guanidine·HCl (30.9 g, 0.323 mol) was added to a solution prepared by dissolving Na metal (7.44 g, 0.323 g-atom) in absolute EtOH (2.0 L). The mixture was stirred rapidly at 25° C. for 30 minutes before 6 (24.7 g, 0.156 mol) was added. The resulting mixture was refluxed with stirring for five days. The EtOH-insoluble product 8 and NaCl were filtered from the boiling mixture. The solid cake was then stirred with boiling EtOH (to insure removal of unchanged 6) before the EtOH-insoluble material was again collected and finally washed thoroughly with $H_2O$, EtOH, and $Et_2O$ in that order to give pure 8; yield 58% (18 g); mass spectrum, m/e 201 (M+1)+, $^1H$ NMR ($Me_2SO-d_6$)-δ2.84 (s, $CH_3$), 6.84 (s, $NH_2$), 7.30 (s, $NH_2$), 8.74 (s, $C^7$—H).

EXAMPLE 7

N-[4-[[(2,4-Diaminopyrido[2,3-d]pyrimidin-6-yl)methyl]-amino]benzoyl]-L-glutamic Acid Diethyl Ester (9). A mixture of 7 (580 mg, 3.12 mmol), diethyl N-(4-aminobenzoyl)-L-glutamate (1.11 g, 3.45 mmol), and Raney Ni (about 3 g damp) in 70% AcOH—$H_2O$ (80 mL) contained in a pressure bottle was shaken on a Parr apparatus at 20°-23° C. under a $H_2$ pressure maintained at 0.98-1.05 $kg/cm^2$ (14-15 psi) for 14 hours. The mixture was treated with Norit, filtered (Celite), and AcOH was removed from the filtrate by evaporation under reduced pressure with the aid of added portions of EtOH. A stirred suspension of the residue in EtOH (20 mL) was treated with cold 2N $Na_2CO_3$ (20 mL), and the mixture was stirred at 5° C. for 30 minutes before the solid was collected and washed on the funnel with $H_2O$, cold EtOH, and $Et_2O$. The dried solid (1.21 g) was stirred several hours with EtOH (50 mL) to remove diethyl N-(4-aminobenzoyl)-L-glutamate whose continued presence was shown by TLC ($CHCl_3$—MeOH, 95:5, UV and ninhydrin detection). The EtOH-insoluble material was collected and washed with $Et_2O$ to give nearly pure product (700 mg), but TLC showed that diethyl N-(4-aminobenzoyl)-L-glutamate was still present to a slight extent. The sample was then dissolved in boiling EtOH (250 mL), and the filtered solution was evaporated to near dryness under reduced pressure. The residue was stirred with EtOH (40 mL), and the suspension was kept in a refrigerator for two days before it was collected and dried in vacuo at 65° C. This material (217 mg, 14% yield) was homogeneous by TLC (MeOH). Spectral data: mass, m/e 496 (M+1)+;

$^1$H NMR (Me$_2$SO-d$_6$), identical with the spectrum reported earlier.

EXAMPLE 8

N-[4-[[2,4-Diamino-5-methylpyrido[2,3-d]pyrimidin-6-yl]methyl]amino]-benzoyl]-L-glutamic Acid Diethyl Ester (10). A stirred solution of 8 (3.00 g, 15.0 mmol) and diethyl N-(4-aminobenzoyl)-L-glutamate (5.33 g, 16.5 mmol) in glacial AcOH (600 mL) containing damp Raney Ni (about 20 g) was kept under H$_2$ at atmospheric pressure for four hours (or one hour after H$_2$ absorption from a gas burette had ceased at about 680 mL). The mixture was then treated with Norit and filtered (Celite mat). AcOH was removed from the filtrate by evaporation under reduced pressure (H$_2$O aspirator, bath to 45° C.) with the aid of added portions of EtOH. Then a solution of the residue in warm EtOH (20 mL) was added in a thin stream to stirred 1N Na$_2$CO$_3$ (200 mL) at 0°-5° C. The mixture was stirred at about 5° C. for 20 minutes longer before the yellow precipitate that formed was collected, washed with H$_2$O, and dried. This crude product (6.1 g ) contained unchanged diethyl N-(4-aminobenzoyl)-L-glutamate (TLC, MeOH), which was removed by repeated treatments with warm Et$_2$O. The Et$_2$O-insoluble material that remained (4.5 g) was dissolved in boiling EtOH (1.2 L). The cloudy solution was clarified (Celite), concentrated (to about 400 mL), and left several hours in a refrigerator while product separated as a yellow solid. This solid (1.79 g) was collected with the aid of EtOH and Et$_2$O. Examination by TLC (CHCl$_3$—MeOH, 2:1) showed a strongly dominant UV-absorbing spot of R$_f$ about 0.5 with slight contamination by material that remained near the origin. The mass spectrum of this sample showed the expected peak of m/e 510 corresponding to (M+1)$^+$ for 10. The sample was dissolved in MeOH (200 mL), and dry-column grade silica (10 g, Silica Woelm TSC, Woelm Pharmaca) was added. Evaporation gave a uniform powdery mixture which was then spread evenly on the surface of a mat of dry Silica Woelm TSC of about 3-cm thickness in a 150-mL fritted-disc funnel (medium porosity). The mat was then eluted at ambient pressure with CHCl$_3$—MeOH (2:1), and portions of eluant of about 30-mL each were collected until TLC showed all the product had been eluted. Several portions contained only the component that gave the UV-absorbing spot of R$_f$ about 0.5. These portions were combined (about 400 mL total) and evaporated to give pure 10 as a beige solid in 15% yield (1.15 g). Spectral data: mass, m/e 510 (M+1)$^+$ and also a weak peak of m/e 496 (not present before the use of MeOH in the workup) attributable to a trace amount of transesterification not detectable in the $^1$H NMR spectrum; $^1$H NMR (Me$_2$SO-d$_6$) δ1.14 (t, C$\overline{H_3}$CH$_2$), 1.16 (t, C$\overline{H_3}$CH$_2$), 2.05 (q, CHCH$_2$), 2.43 (t, C$\overline{H_2}$CH$_2$CO), 2.68 (s, 5-CH$_3$), 3.9–4.2 (two $\overline{q}$, CH$_3$CH$_2$O), 4.2–4.5 (overlapping m, NHC$\overline{H}$CO, CH$_2$N), 6.$\overline{24}$ (s, NH$_2$), 6.50 (t, CH$_2$NH), 6.68 and 7.70 (two d, C$_6$H$_4$), 7.00 (s, NH$_2$), 8.25 (d, CONHCH), 8.50 (s, 7-H).

EXAMPLE 9

N-[4-[[2,4-Diamino-5-methylpyrido[2,3-d]pyrimidine-6-yl]methyl]amino]-benzoyl]-L-glutamic Acid (12, 5-Methyl-5-deazaaminopterin). A stirred solution of 10·5H$_2$O (1.7 g, 2.6 mmol) in Me$_2$SO (30 mL) was treated under N$_2$ with 1N NaOH (5.25 mL). The solution that formed was kept under N$_2$ in a stoppered flask at 20°-23° C. for six hours and was then evaporated to dryness in vacuo (about 0.1 mm, bath to 30° C.). The yellow solid that remained was dissolved in H$_2$O (50 mL), and the clear solution was immediately treated with 1N HCl with stirring to produce pH 3.6 and cause precipitation of 12. The mixture was kept several hours in an ice-H$_2$O bath before the solid was collected. The $^1$H NMR spectrum of this material was as expected for 12 except for retention of Me$_2$SO. An attempt to remove the Me$_2$SO by stirring the dried solid with Et$_2$O was ineffective. The Me$_2$SO was removed by reprecipitation as follows. The pulverized solid (0.91 g) was stirred with H$_2$O under N$_2$, and 1N NaOH was added dropwise until the pH remained near 8. Solution occurred, and the product was then reprecipitated by careful addition of 1N HCl to pH 3.6. After the mixture had been kept several hours at 0°-5° C., the beige solid was collected, washed with cold H$_2$O, and dried in vacuo; yield 82% (0.83 g). Spectral data: mass, m/e 454 (M+1)$^+$; UV, 0.1N HCl, 224 (39.6), 298 (21.5); pH 7, 222 (36.0), 282 (26.7); 0.1N NaOH, 223 (34.1), 283 (27.2), 340 plateau (8.69); $^1$H NMR (Me$_2$SO-d$_6$) 2.02 (m, CHCH$_2$), 2.30 (m, CH$_2$CO$_2$H), 2.72 (s, CH$_3$), 4.34 (m, NHC$\overline{H}$CO, CH$_2$N), 6.$\overline{53}$ (s, NH$_2$), 6.66 and 7.70 (two d, C$_6$H$_4$), 7.36 (s, $\overline{NH_2}$), 8.02 (d, CONHCH), 8.54 (s, 7-H). Analysis by high-performance L$\overline{C}$ showed a purity level of at least 98% with respect to UV-absorbing material.

EXAMPLE 10

2,4-Diamino-5-methylpyrido[2,3-d]pyrimidine-6-carboxaldehyde (13). A solution of 8 (2.00 g, 10.0 mmol) in HCO$_2$H (50 mL of 95–97%) was added in a thin stream with stirring to Raney Ni (about 14 g damp). The mixture was stirred at 75°–80° C. (bath temperature) for 1.5 hours, then filtered while hot, and the solid on the funnel was washed with small portions of warm HCO$_2$H until the washings were colorless. The filtrate was evaporated to dryness under reduced pressure with the aid of added portions of EtOH. The solid residue was then dissolved in hot H$_2$O (200 mL), and the solution was clarified (Norit, Celit) to give an orange filtrate, which, when neutralized with 1N NaOH to pH 7, gave a yellow solid; yield 1.62 g. Spectral data: mass, dominant peak of m/e 204 (M+1)$^+$ for 13; lesser peak of m/e 206 (M+1)$^+$ for the hydroxymethyl compound 14; $^1$H NMR (Me$_2$SO-d$_6$) δ2.98 (s, CH$_3$), 8.90 (s, C$^7$—H), 10.23 (CHO). HPLC assay indicated the mixture to be at least 87% 13 and 4% 14 with remaining material unidentified. Another run (3.3 g of 8) gave similar results (2.73 g of 13 suitable for conversion to 14 as described below).

EXAMPLE 11

2,4-Diamino-5-methylpyrido[2,3-d]pyrimidine-6-methanol (14). NaBH$_4$ (500 mg, 13.2 mmol) was added in portions during a 10 minute interval to a stirred suspension of crude 13 (2.73 g), in MeOH (500 mL) at 20°-23° C. Stirring was continued for two hours, then NaBH$_4$ (500 mg) was again added as before. After the mixture had been stirred overnight, HPLC (acetate buffer of pH 3.6-MeOH, 9:1) showed the conversion of 13 to the more polar 14 was complete. After removal of the MeOH by evaporation, the residue was stirred with H$_2$O (90 mL) and treated with 1N HCl to lower the pH to 8.0 (from 11.3 initially). This mixture was stirred while being heated at about 70° C. (bath temperature) for 20 minutes. The solid filtered from the cooled mixture amounted to 2.63 g and was used without further purification in the conversion to crude 15 described below. Spectral data: mass, m/e 206 (M+1)+; ¹H NMR (Me₂SO-d₆) δ2.68 (s, CH₃), 4.52 (s, CH₂), 8.48 (s, C⁷—H).

EXAMPLE 12

6-(Bromomethyl)-2,4-diamino-5-methylpyrido[2,3-d]-pyrimidine Hydrobromide (15). Powdered 14 (205 mg, 1.0 mmol) was added to a stirred suspension of (C₆H₅)₃PBr₂⁴⁰ (1.39 g, 3.3 mmol) in Me₂NAc (4 mL). After the mixture had been stirred at 20°-23° C. for two hours, the clear red solution that had formed was treated with C₆H₆ (40 mL) to cause precipitation of a red solid. The clear liquid phase was removed by decantation, and the solid was stirred successively with portions of C₆H₆ and Et₂O (40 mL of each). Residual solvent was removed by evaporation, and the residue was dissolved in the minimum volume of 48% HBr at 20°-23° C. The solution was kept at that temperature for 30 minutes and was then added to MeCN (50 mL) to give a tan solid precipitate. The mixture was stirred in an ice-H₂O bath for 30 minutes before the solid was collected wit the aid of MeCN and Et₂O, then dried in vacuo to give the bromomethyl compound (177 mg) suitable for use in the preparations of 18 and 19 described below. Spectral data: mass, m/e 268 and 270 (M+1)+ for C₉H₁₀BrN₅.

EXAMPLE 13

N-[4-(Methylamino)benzoyl]-L-glutamic acid dimethyl ester (16) was prepared in two steps as follows:

Step A. N-[4-[[(Benzyloxy)carbonyl]methylamino]-benzoyl]-L-glutamic acid dimethyl ester was prepared from 4-[[(benzyloxy)-carbonyl]methylamino]-benzoyl chloride and L-Glu-diMe·HCl (dimethyl L-glutamate hydrochloride) using essentially the same procedure reported for the preparation of the corresponding diethyl ester from the in situ-prepared aroyl chloride by Fu et al, *J. Med Chem*, Vol. 30, page 1277 (1975). The yield of pure (benzyloxy)carbonyl derivative, mp 82° C. (Kofler Heizbank), was 89% (5.9 g from a 15.0-mmol run); homogeneous by TLC (CHCl₃—MeOH, 95:5).

Step B. Conversion of 16. A solution of the (benzyloxy)carbonyl derviative (5.00 g, 11.3 mmol) in MeOH (75 mL) containing 30% Pd on C (0.5 g) was stirred under H₂ (over H₂O in a gas burette) at ambient conditions for two hours or until H₂ uptake had ceased (about 255 mL). The catalyst was removed by filtration, and the viscous oil that remained following evaporation was homogeneous by TLC (CHCl₃—MeOH, 95:5, detection by UV and ninhydrin); yield 90% (3.4 g). This material was used as such for the conversion to 18 described below. After about two months, the oil had mostly solidified. A sample for analysis after trituration with ligroin had mp 54°-55° C.

EXAMPLE 14

N-[4-[[(2,4-Diamino-5-methylpyrido[2,3-d]pyrimidin-6-yl)methyl]methylamino]benzoyl]-L-glutamic Acid Dimethyl Ester (18). The crude bromomethyl compound 15 (175 mg) was added to a stirred solution of 16 (185 mg, 0.55 mmol) in Me₂NAc (3 mL). Solution occurred within five minutes, and a TLC (CHCl₃—MeOH, 3:1) spot of R_f about 0.4 due to a reaction product was strongly evident after six hours. The solution was kept at 22°-25° C. for 24 hours, warmed at 50°-55° C. for four hours, then left 16 hours longer at 23°-25° C. before it was added to EtOAC (40 mL) with stirring. The tan solid that formed was collected, dried (217 mg), and dissolved in H₂O (5 mL). This solution was added to 1N Na₂CO₃ (5 mL) with stirring to give a brown solid (112 mg). This crude material was stirred in boiling MeOH (methyl alcohol) (25 mL), and the mixture was clarified by filtration from a small portion of insoluble material. The filtrate was mixed with dry-column grade silica (500 mg, Silica Woelm TSC, Woelm Pharmaca), and the mixture was evaporated. The residue was distributed on a mat of the silica gel described above about 2.5 cm thick contained in a 15-mL funnel of medium porosity. The mat was then eluted at ambient pressure with CHCl₃—MeOH (2:1). Early fractions contained unchanged 16. Intermediate fractions contained only 18 as evidenced by TLC examination. These fractions were evaporated to give 18 as a beige solid; yield 67 mg (approximately 27% if based on 0.50 mmol of 15). Spectral data: mass, m/e 496 (M+1)+. This material was suitable for the conversion to pure 20 described below. Another run like that above but using 740 mg of crude 15 and left 5.5 days at 22°-25° C. produced 407 mg of 18 homogeneous by TLC.

EXAMPLE 15

N-[4-[[2,4-Diamino-5-methylpyrido[2,3-d]pyrimidin-6-yl)methyl]methylamino]benzoyl-L-glutamic Acid (20), 5-Methyl-5-deazamethotrexate).

A. From 18. A solution of 18 (396 mg, 0.8 mmol) in MeOH (60 mL) containing 1N NaOH (1.68 mL) was kept at 22°-25° C. for 48 hours, then at 45°-50° C. for one hour, and finally 17 hours longer at 22°-25° C. while the progress of the saponification was followed by HPLC. The solution was evaporated to dryness, and the solid residue was dissolved in H₂O (20 mL). This solution was kept at 22°-25° C. for one hour, then at 45° C. for 30 minutes. HPLC showed ester hydrolysis to be complete. The solution was filtered (Norit, Celite), then carefully treated with 1N HCl to pH 3.8 giving 20 as a light yellow solid. After several hours in an ice-H₂O bath, the precipitate was collected with the aid of cold H₂O and dried in vacuo; yield 74% (308 mg). Spectral data: mass, m/e 468 (M+1)+; UV, 0.1N HCl, 227 (39.7), 310 (22.4); pH 7, 227 (37.5), 307 (28.6); 0.1N NaOH, 228 (36.5), 306 (27.9); ¹H NMR (Me₂SO-d₆) δ1.9-2.2 (br m, CHCH₂CH₂), 2.30 (m, CH₂CO₂H), 2.63 (s, CH₃C), 3.02 (s, CH₃N), 4.34 (m, NHCHCO), 4.66 (s, CH₂N), 6.73 and 7.75 (two d, C₆H₄), 8.10 (d, CONHCH), 8.13 (s, 7-H). Analysis by HPLC showed the purity level to be at least 98% with respect to UV-absorbing material.

B. From 12. A stirred suspension of 12·2.2H₂O (150 mg, 0.304 mmol) in O₂-free H₂O (8 mL) was treated under N₂ with sufficient 1N NaOH to cause solution. The pH was then adjusted to 6.4 using 1N HCl. A solution of CH₂O in H₂O (93 μL of 37%, sp. gr. 1.08, 3.3 mmol) was added followed by NaBH₃CN (31.2 g, 0.496 mmol). The pH of the solution was kept at 6.4 by addition of 1N HCl as required during the next hour. The solution was kept under N₂ while the progress of the conversion was followed by HPLC and observed to be complete after 21 hours at 22°-25° C. The clarified (Norit, Celite) solution was acidified to pH 3.8 with 1N HCl to give 20 (130 mg). A reprecipitation from a solution of pH 8.5 by addition of 1N HCl to pH 3.8 afforded pure 20 in 64% yield (96 mg) identical (HPLC) with the sample described under method A above.

EXAMPLE 16

N-[4-[[(2,4-Diamino-5-methylpyrido[2,3-d]pyrimidin-6-yl)methyl]ethylamino]benzoyl-L-glutamic Acid Diethyl Ester (19). Alkylation of diethyl N-[4-(ethylamino)benzoyl]-L-glutamate (17) (648 mg, 1.85 mmol) with the crude bromomethyl compound 15 (636 mg, prepared as described above) in $Me_2NAc$ (11 mL) during six days at 22°–25° C. followed by a workup like that described for 18 (except that 9:1 $CHCl_3$—MeOH was used in the elution from silica gel) led to a sample of 19 (67 mg, about 8% yield) homogeneous by TLC; mass spectrum, m/e 538 $(M+1)^+$.

EXAMPLE 17

N-[4-[[(2,4-Diamino-5-methylpyrido[2,3-d]pyrimidin-6-yl)methyl]ethylamino]benzoyl-L-glutamic acid (21, 5-Methyl-5-deaza-10-ethylaminopterin) was prepared by saponification of 19 as described for the conversion of 18 to 20; yield 97% (56 mg from 60 mg, 0.109 mmol), of $19 \cdot 0.6H_2O$, homogeneous by HPLC. Spectral data: mass, m/e 482 $(M+1)^+$; UV, 0.1N HCl, 228 (40.8), 313 (17.1; pH 7, 227 (39.2), 308 (30.2); 0.1N NaOH, 228 (36.0), 308 (29.0).

TABLE 1

Elemental Analysis

| Compound No. | Molecular Formula | % C | Calcd. Found % H | % N |
|---|---|---|---|---|
| 4 | $C_8H_5ClN_4$ | 48.89 | 2.62 | 29.09 |
|   |   | 49.13 | 2.65 | 29.44 |
| 5 | $C_7H_4N_4$ | 58.33 | 2.80 | 38.89 |
|   |   | 58.51 | 2.89 | 38.98 |
| 6 | $C_8H_6N_4$ | 60.74 | 3.82 | 35.43 |
|   |   | 60.79 | 3.83 | 35.26 |
| 7 | $C_8H_6N_6 \cdot 0.65H_2O$ | 48.55 | 3.72 | 42.47 |
|   |   | 48.32 | 3.59 | 42.87 |
| 8 | $C_9H_8N_6$ | 53.99 | 4.03 | 41.98 |
|   |   | 53.88 | 4.02 | 42.02 |
| 9 | $C_{24}H_{29}N_7O_5$ | 58.17 | 5.90 | 19.79 |
|   |   | 57.88 | 6.10 | 19.41 |
| 10 | $C_{25}H_{31}N_7O_5 \cdot 0.5H_2O$ | 57.90 | 6.22 | 18.91 |
|   |   | 57.78 | 5.92 | 19.08 |
| 12 | $C_{21}H_{23}N_7O_5 \cdot 2.2H_2O$ | 51.15 | 5.59 | 19.88 |
|   |   | 51.01 | 5.60 | 20.18 |
| (Benzyloxy)-carbonyl deriv. of 16 | $C_{23}H_{26}N_2O_7$ | 62.43 | 5.92 | 6.33 |
|   |   | 62.10 | 6.07 | 6.46 |
| 16 | $C_{15}H_{20}N_2O_5$ | 58.43 | 6.54 | 9.09 |
|   |   | 58.07 | 6.75 | 9.09 |
| 18 | $C_{24}H_{29}N_7O_5 \cdot 0.75H_2O$ | 56.62 | 6.24 | 19.26 |
|   |   | 56.69 | 5.90 | 18.66 |
| 19 | $C_{27}H_{35}N_7O_5 \cdot 0.6H_2O$ | 59.13 | 6.65 | 17.88 |
| 20 (from 18) | $C_{22}H_{25}N_7O_5 \cdot 3H_2O$ | 59.12 50.66 | 6.77 5.99 | 17.78 18.80 |
|   |   | 50.27 | 5.84 | 18.96 |
| 20 (from 12) | $C_{22}H_{25}N_7O_5 \cdot 1.65H_2O$ | 53.14 | 5.71 | 19.72 |
|   |   | 52.87 | 5.86 | 19.81 |
| 21 | $C_{23}H_{27}N_7O_5 \cdot 2.8H_2O$ | 51.93 | 6.18 | 18.43 |
|   |   | 52.07 | 6.05 | 18.34 |

Biological Studies. The inhibitory effects of 11, 12, 20, 21 and dMTX on DHFR from L1210 cells, their effect on growth of L1210 cells in culture, and their transport characteristics with respect to these cells are listed in Table 2 with results from AMT and MTX. Each analogue is at least as potent in the inhibition of DHFR as the parent compound. 5-Me-5-dMTX (20) and 5-Me-10-Et-5-dAMT (21) are 10 times as potent in the L1210 cell growth inhibition test as MTX. The remaining 2,4-diamino types gave essentially the same $IC_{50}$ values as the respective parent compounds. In the transport studies (Table 2), each analogue tested showed essentially the same influx and efflux characteristics as the respective parent compounds.

Initial rates of polyglutamate accumulation in L1210 cells of the analogue listed in Table 2 (except 5-Me-10-Et-5-dAMT, 21) were determined under conditions of comparable rates of drug entry. There appeared to be no correlation between the rate of anabolism to polyglutamate forms of 5-Me-5-dMTX (20) and its greater cytotoxicity compared with MTX. Among the analogues the rates varied in the order AMT>5-Me-5-dAMT>5-dAMT>MTX>5-dMTX>5-Me5-dMTX.

Results from analogue comparison studies against P388/0 and P388/MTX in vivo are summarized in Table 3. Against P388/0, each of the five analogues tested showed significant activity comparable to that of MTX. 5-Me-5-dMTX appears to correlate with the $IC_{50}$ values from the cell growth inhibition assay. In the parallel comparison tests versus MTX-resistant P388, none of the analogues showed activity greater than that of MTX.

Table 4 sets forth a comparison of antitumor effects of methotrexate and 20 against the EO771 mammary adenocarcinoma in mice.

TABLE 2

Biochemical Properties of AMT, MTX, and 5-Deaza and 5-Methyl-5-deaza Analogues in L1210 Cells

| Compound | DHFR inhibn (a) Ki (n = 3) ± SE (pM) | Cell Growth inhibn (a) $IC_{50}$ (n = 4) ± SE (nM) | Mediated Transport (a) (n = 3–4) influx Km (μM) + SE | Mediated Transport (a) (n = 3–4) efflux k (min⁻¹) + SE | Rate of net polyglutamate formation (b) (pM/min/g dry wt) |
|---|---|---|---|---|---|
| AMT | 3.55 ± 0.4 | 0.72 ± 0.1 | 1.2 ± 0.3 | 0.31 ± 0.04 | 165 |
| 5-dAMT (11) | 3.65 ± 0.7 | 0.63 ± 0.07 | 1.1 ± 0.2 | 0.30 ± 0.04 | 84.2 |
| 5-Me-5-dAMT (12) | 2.93 ± 0.1 | 1.29 ± 0.2 | 1.2 ± 0.2 | 0.26 ± 0.05 | 98.3 |
| MTX | 5.48 ± 0.6 | 2.55 ± 0.3 | 3.3 ± 0.7 | 0.33 ± 0.06 | 56.3 |
| 5-dMTX | 5.26 ± 0.7 | 2.85 ± 0.3 | 4.0 ± 0.5 | 0.28 ± 0.04 | 48.8 |
| 5-Me-5-dMTX (20) | 2.12 ± 0.4 | 0.24 ± 0.03 | 3.2 ± 0.4 | 0.31 ± 0.05 | 42.9 |
| 5-Me-10-Et-5-dAMT (21) | 2.64 ± 0.3 | 0.26 ± 0.02 | 3.3 ± 0.5 | 0.29 ± 0.04 | — |

(a) Methods are described by Sirotnak et al, "Molecular Actions and Targets for Cancer Chemotherapy Agents", Sartorelli, A.C. Ed., Academic Press., New York, pps. 349–383 (1981); Sirotnak et al, Biochem. Pharmacol., Vol. 29, p. 3293 (1980); and Sirotnak et al, Cancer Res., Vol. 36, p. 1151 (1976).
(b) See Samuels et al, Cancer Res., Vol. 45, p. 1488 (1985).

TABLE 3

Comparison of the Response of Murine P388/0 and P388/MTX to Treatment with MTX and 5-Deaza and 5-Me-5-deaza Analogues of AMT and mTX Treatment: ip; qd 1–5

| Compound | P388/O[a] Optimal dose (mg/kg) | survival time (days) | % T/C | P388/MTX[a] Optimal dose (mg/kg) | survival time (days) | % T/C |
|---|---|---|---|---|---|---|
| Control |  | 10.8 |  |  | 17.2 |  |
| MTX | 4 | 19.7 | 182 | 3.5 | 20.3 | 118 |
| 9 | 1 | 16.2 | 151 | 1 | 20.8 | 120 |
| 11 | 0.5 | 15.8 | 146 | 2 | 21.8 | 126 |
| 12 | 0.5 | 16.4 | 151 | 0.5 | 20.8 | 120 |
| 5-dMTX | 4 | 18.0 | 166 | 4 | 20.3 | 118 |
| 20 | 1 | 19.7 | 182 | 0.25 | 20.8 | 120 |

[a]Implant: ip, $10^6$ cells; method described by Geran et al, Cancer Chemother. Rep. Part 3, Vol. 3 (2) (1972).

TABLE 4

A Comparison of Antitumor Effects of Methotrexate and 5-Methyl-5-Deazamethotrexate (20) Against the EO771 Mammary Adenocarcinoma. Average of Two Separate Experiments (5 Mice/Group) ± SE of the Mean.

| Compound | dose[1] (mg/kg) | AWC[2] (g) | toxic deaths[3] total | ave. tumor vol.[4] mm³ | T/C | tumor free[5] total |
|---|---|---|---|---|---|---|
| control | — | 20.85 |  | 225 ± 60 | 1.00 | 0/14 |
| MTX | 1.5 | +0.9 | 0/10 | 102 ± 32 | 0.60 | 1/10 |
| MTX | 3.0 | −0.2 | 0/10 | 108 ± 24 | 0.61 | 1/10 |
| MTX | 6.0 | −2.1 | 4/10 | 22 ± 5 | 0.12 | toxic |
| 20 | 0.375 | −0.4 | 0/10 | 50 ± 16 | 0.25 | 0/10 |
| 20 | 0.75 | +0.2 | 0/10 | 35 ± 10 | 0.13 | 1/10 |
| 20 | 1.5 | −2.5 | 0/10 | 4 ± 2 | 0.03 | 6/10 |
| 20 | 3.0 | −3.6 | 5/6 | 3 ± 1 | 0.02 | toxic |

[1]given once per day for five days starting one day after tumor implantation
[2]average weight change on day 7 (one day after cessation of therapy)
[3]assessed on day 7, 14 or 21
[4]assessed on day 7 (4/3 πr³) T/C = treated/control
[5]assessed on day 7 (one day after cessation of therapy)

What is claimed is:

1. A compound selected from the group consisting of 5-methyl-5-deazamethotrexate and 5-methyl-5-deaza-10-ethylaminopterin.

2. A compound as defined in claim 1 which is 5-methyl-5-deazamethotrexate.

3. A compound as defined in claim 1 which is 5-methyl-5-deaza-10-ethylaminopterin.

4. An intermediate useful in the preparation of 5-methyl-5-deazamethotrexate selected from the group consisting of N-[4-[[2,4-diamino-5-methylpyrido[2,3-d]pyrimidin-6-yl)methyl]amino]-benzoyl]-L-glutamic acid diethyl ester and N-4-[[2,4-dimino-5-methylpyrido[2,3-d]pyrimidine-6-yl)methyl]amino]-benzoyl]-L-glutamic acid.

5. An intermediate as defined in claim 4 which is N-[4-[[2,4-diamino-5-methylpyrido[2,3-d]pyrimidin-6-yl)methyl]amino]-benzoyl]-L-glutamic acid diethyl ester.

6. An intermediate as defined in claim 4 which is N-[4-[[2,4-diamino-5-methylpyrido[2,3-d]pyrimidin-6-yl)methyl]amino]-benzoyl]-L-glumatic acid.

7. An intermediate useful in the preparation of 5-methyl-5-deazamethotrexate and 5-methyl-5-deaza-10-ethylaminopterin selected from the group consisting of 2,4-diamino-5-methylpyrido[2,3-d]pyrimidine-6-carbonitrile, 2,4-diamino-5-methylpyrido[2,3-d]pyrimidine-6-carboxaldehyde, 2,4-diamino-5-methylpyrido[2,3-d]pyrimidine-6-methanol, 6-(bromomethyl)-2,4-diamino-5-methylpyrido[2,3-d]pyrimidine hydrobromide, N-[4-[[(2,4-diamino-5-methylpyrido[2,3-d]pyrimidin-6yl)methyl]methylamino]benzoyl]-L-glutamic acid diemthyl ester, and N-[4-[[(2,4-diamino-5-methylpyrido[2,3-d]pyrimidin-6-yl)methylethylamino]-benzoyl-L-glutamic acid diethyl ester.

8. An intermediate as defined in claim 6 which is 2,4-diamino-5-methylpyrido[2,3-d]pyrimidine-6-carbonitrile.

9. An intermediate as defined in claim 7 which is 2,4-diamino-5-methylpyrido[2,3-d]pyrimidine-6-carboxaldehyde.

10. An intermediate as defined in claim 7 which is 2,4-diamino-5-methylpyrido[2,3-d]pyrimidine-6-methanol.

11. An intermediate as defined in claim 7 which is 6-(bromomethyl)-2,4-diamino-5-methylpyrido[2,3-d]pyrimidine hydrobromide.

12. An intermediate as defined in claim 7 which is N-[4-[[(2,4-diamino-5-methylpyrido[2,3-d]pyrimidin-6-yl)methyl]methylamino]benzoyl]-L-glutamic acid dimethyl ester.

13. An intermediate as defined in claim 7 which is N-[4-[[(2,4-diamino-5-methylpyrido[2,3-d]pyrimidin-6yl)methylethylamino]benzoyl-L-glutamic acid diethyl ester.

* * * * *